United States Patent [19]

Wilson, II

[11] 4,399,148

[45] Aug. 16, 1983

[54] HYDROXYARYLALKYLENEAMINOARYL CARBAMATES AND DERIVATIVES THEREOF USEFUL AS INSECTICIDAL COMPOSITIONS

[75] Inventor: Charles A. Wilson, II, Charleston, W. Va.

[73] Assignee: Union Carbide Corporation, Danbury, Conn.

[21] Appl. No.: 247,369

[22] Filed: Mar. 25, 1981

[51] Int. Cl.$^3$ .................. C07C 125/067; A01N 47/22
[52] U.S. Cl. .................................. 424/285; 424/287; 424/289; 424/294; 424/295; 424/300; 542/422; 542/423; 544/159; 549/470; 260/429 C; 260/429.9; 260/438.1; 260/438.5 R; 260/439 R; 260/448 B; 260/465 D; 560/133; 560/134
[58] Field of Search ................ 560/133, 134; 549/470; 542/422, 423; 544/159; 260/438.1, 465 D, 429 C, 439 R, 438.1, 438.5 R, 448 B, 429.9; 424/289, 285, 287, 294, 295, 300

[56] References Cited

U.S. PATENT DOCUMENTS 3,012,068 12/1961 Shulgin ............................... 260/482

FOREIGN PATENT DOCUMENTS 123053 11/1976 German Democratic Rep. .

OTHER PUBLICATIONS

Hodnett et al., J. Med. Chem., (1971), vol. 14, No. 11, pp. 1121–1123.

Primary Examiner—Henry R. Jiles
Assistant Examiner—Bernard Dentz
Attorney, Agent, or Firm—G. L. Coon; J. A. Shedden

[57] ABSTRACT

This invention relates to novel hydroxyarylalkyleneaminoaryl carbamate compounds and derivatives thereof and to their preparation. This invention is also directed to insecticidal compositions comprising an acceptable carrier and an insecticidally effective amount of a hydroxyarylalkyleneaminoaryl carbamate compound or derivative of this invention as well as to a method of controlling insects by subjecting them to an insecticidally effective amount of a hydroxyarylalkyleneaminoaryl carbamate compound or derivative of this invention.

90 Claims, No Drawings

HYDROXYARYLALKYLENEAMINOARYL CARBAMATES AND DERIVATIVES THEREOF USEFUL AS INSECTICIDAL COMPOSITIONS

FIELD OF THE INVENTION

This invention relates to novel hydroxyarylalkyleneaminoaryl carbamate compounds and derivatives thereof which exhibit superior toxicity as insecticides, particularly superior systemic toxicity as aphicides.

BACKGROUND OF THE INVENTION

Of the large number of commercial synthetic insecticides available today, relatively few exhibit systemic activity, that is, the ability to be absorbed by the vascular system of the plant to be protected and to be translocated to the parts of the plant attacked by insects. Once ingested by the insect, the systemic insecticide acts as a strong stomach poison and thus provides efficient insect control. Moreover, not all commercial synthetic insecticides having systemic activity possess desirable broad spectrum activity against a wide variety of insects.

A major advantage inherent in the mode of action of a systemic insecticide and not shared by contact poisons is that beneficial insects which do not feed on the protected plants are not harmed by application of the systemic toxicant. In addition, systemic materials are generally not subject to loss of activity caused by weathering, e.g., heavy rain and strong sunlight, and, consequently, relatively few applications of the insecticide are required for long lasting insect control.

The compounds of this invention possess the major attributes of a systemic insecticide, viz., good systemic properties and high stomach toxicity, to an exceptional degree and also exhibit broad spectrum activity against a wide variety of insects. Nowhere in the prior art currently known to us is there any disclosure or suggestion of the discovery of the novel hydroxyarylalkyleneaminoaryl carbamate compounds or derivatives of the present invention which exhibit superior toxicity as insecticides, particularly superior systemic toxicity as aphicides. U.S. Pat. No. 3,012,068 discloses Schiff base carbamate esters prepared by (1) the reaction of an appropriate aldehyde compound with an appropriate amine compound, i.e., (a) a benzaldehyde compound with an aminophenol compound, or (b) a hydroxybenzaldehyde compound with an aniline compound to produce an intermediate Schiff base phenol and water followed by (2) the reaction of the intermediate Schiff base phenol with methyl isocyanate in the presence of a basic catalyst. However, U.S. Pat. No. 3,012,068 neither discloses, suggests nor exemplifies the hydroxyarylalkyleneaminoaryl carbamate compositions and derivatives of the present invention. In fact, the hydroxyarylalkyleneaminoaryl carbamate compositions and derivatives of the present invention are specifically excluded from the scope of U.S. Pat. No. 3,012,068 in that the aldehydes disclosed for reaction (a) above are restricted to no hydroxy substituents (column 2, lines 6 and 7). The hydroxyarylalkyleneaminoaryl carbamate compositions and derivatives of the present invention as exemplified by 4-(2-hydroxybenzylideneamino)-3,5-dimethylphenyl methylcarbamate unexpectedly exhibit superior systemic toxicity as aphicides in comparison with the Schiff base carbamate esters disclosed in U.S. Pat. No. 3,012,068.

SUMMARY OF THE INVENTION

The compounds of this invention are hydroxyarylalkyleneaminoaryl carbamates and derivatives thereof which can be depicted structurally as follows:

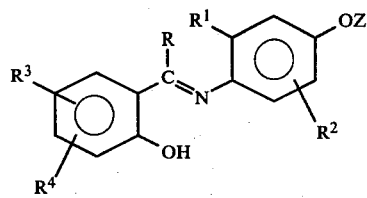

wherein Z is hydrogen or

R and $R^1$ are individually hydrogen or alkyl; $R^2$ is hydrogen, halo, alkyl, alkoxy, alkenyl, alkylthioalkyl or a alkenyloxy provided that when $R^1$ and $R^2$ are alkyl or alkoxy and located adjacent to each other, then $R^1$ and $R^2$ together may form a three-to-five-membered bridge consisting of carbon atoms or carbon and oxygen atoms in which the carbon atoms may be optionally substituted with alkyl and provided further that when the bridge consists of four carbon atoms, the resulting six-membered ring may optionally be aromatic or substituted aromatic; $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio provided that when $R^3$ and $R^4$ are alkyl or alkoxy and located adjacent to each other, then $R^3$ and $R^4$ together may form a bridge of from three to five carbon atoms which may be optionally substituted with alkyl and provided further that when the bridge consists of four carbon atoms, the resulting six-membered ring may optionally be aromatic or substituted aromatic; and $R^5$ and $R^6$ are individually hydrogen or alkyl provided that when $R^5$ is alkyl, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoarylcarbamoylsulfenyl (i.e. hydroxyarylalkyleneaminoaryloxycarbonylaminoothio), hydroxyarylalkyleneaminoarylcarbamoylthiosulfenyl (i.e. hydroxyarylalkyleneaminoaryloxycarbonylaminoothiosulfenyl), alkylsulfenyl, phenylsulfenyl, alkylthiosulfenyl or phenylthiosulfenyl, wherein the permissible substituents are one or more fluoro, chloro, bromo, cyano, aroyl, nitro, alkyl, alkanoyl, alkoxy, phenyl, phenoxy or trihalomethyl substituents in any combination. It is understood that the above radicals containing the sulfenyl moiety may instead contain a sulfinyl moiety. The derivatives of the hydroxyarylalkyleneaminoaryl carbamates within the scope of this invention include, for example, the metal salts thereof.

This invention further provides an insecticidal composition comprising an acceptable carrier and as the active toxicant an insecticidally effective amount of a hydroxyarylalkyleneaminoaryl carbamate compound or derivative thereof as described hereinabove.

This invention also relates to a method of controlling insects which comprises subjecting them to an insecticidally effective amount of a hydroxyarylalkyleneaminoaryl carbamate compound or derivative thereof as described hereinabove.

This invention still further relates to a method of preparing hydroxyarylalkyleneaminoaryl carbamates and derivatives thereof as described hereinabove which comprises (1) reacting a hydroxybenzaldehyde and an aminophenol to form an imine bisphenol intermediate and (2) reacting the imine bisphenol intermediate and an isocyanate to form the hydroxyarylalkyleneaminoaryl carbamates and derivatives thereof of this invention.

DESCRIPTION OF PREFERRED EMBODIMENTS

The hydroxyarylalkyleneaminoaryl carbamates and derivatives thereof of this invention contain, as an essential substituent, a hydroxy group located at the 2-position on the aryl ring of the arylalkyleneamino group as structurally depicted hereinabove. The imine bisphenol intermediate compounds of this invention are those of the above formula in which Z is hydrogen and R, $R^1$, $R^2$, $R^3$, $R^4$, $R^5$ and $R^6$ are as described above. The hydroxyarylalkyleneaminoaryl carbamates and derivatives of this invention are those of the above formula in which Z is

and R, $R^1$, $R^2$, $R^3$, $R^4$, $R^5$ and $R^6$ are as described above. The imine bisphenol intermediate compounds are useful in the preparation of the insecticidally active hydroxyarylalkyleneaminoaryl carbamate compounds and derivatives thereof.

The preferred compounds of this invention are those of the above formula wherein R and $R^1$ are individually hydrogen or alkyl having from 1 to 6 carbon atoms inclusive. Most preferably, R and $R^1$ are individually hydrogen or alkyl having from 1 to 4 carbon atoms inclusive. It is preferred that $R^2$ is hydrogen, halo or alkyl, alkoxy, alkenyl, alkylthioalkyl or alkenyloxy having from 1 to 6 carbon atoms inclusive, most preferably from 1 to 4 carbon atoms inclusive. When $R^1$ and $R^2$ are alkyl or alkoxy having from 1 to 6 carbon atoms inclusive and located adjacent to each other, then preferably $R^1$ and $R^2$ together may form a three-to-five-membered bridge consisting of carbon atoms or carbon and oxygen atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic. 2,3-Dihydro-2,2-dimethyl-4-(2-hydroxybenzylideneamino)benzofuran-7-yl methylcarbamate is a preferred compound containing a 3-membered bridge with carbon and oxygen atoms and 4-(2-hydroxybenzylideneamino)naphth-1-yl methylcarbamate is a preferred compound containing a 4-membered aromatic bridge. $R^3$ and $R^4$ are preferably individually hydrogen, halo, nitro, cyano, hydroxy, unsubstituted or aliphatically substituted phenyl or phenoxy, alkyl, alkoxy, alkylcarbamoyloxy or alkylthio having from 1 to 6 carbon atoms inclusive, most preferably from 1 to 4 carbon atoms inclusive. When $R^3$ and $R^4$ are alkyl or alkoxy having from 1 to 6 carbon atoms inclusive and located adjacent to each other, then preferably $R^3$ and $R^4$ together may form a bridge of from three to five carbon atoms which may be optionally substituted with alkyl having from 1 to 4 carbon atoms inclusive and provided further that when the bridge consists of four carbon atoms, the resulting six-membered ring may optionally be aromatic or substituted aromatic. 3-Isopropyl-4-(2-hydroxy-1-naphthylmethyleneamino)phenyl methylcarbamate is a preferred compound containing a 4-membered aromatic bridge. It is preferable that $R^5$ and $R^6$ are individually hydrogen or alkyl having from 1 to 6 carbon atoms inclusive, most preferably from 1 to 4 carbon atoms inclusive, provided that when $R^5$ is alkyl having from 1 to 6 carbon atoms inclusive, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoarylcarbamoylsulfenyl, hydroxyarylalkyleneaminoarylcarbamoylthiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination. As described hereinabove, the radicals of $R^6$ containing the sulfenyl moiety may instead contain a sulfinyl moiety.

The metal salts of hydroxyarylalkyleneaminoaryl carbamates of this invention preserve the activity, or substantially the activity, of the parent or unsalified compound, and also have no additional, undesirable effect on the plant being treated. It is to be understood that in some instances such salts may display an enhanced activity due to their being more readily assimilated by the plant being treated. Examples of the preferably employed salts are the metal salts of the acid function, such as the salts with sodium, potassium, lithium, magnesium, calcium, molybdenum, chromium, aluminum, manganese, iron, cobalt, nickel, copper and zinc. The most preferred metal salt of the acid function is the salt with copper (II). There are a very large number of acceptable salts suitable for use in this invention, as would readily be appreciated by one skilled in the art.

Illustrative of the preferred imine bisphenol intermediate compounds of this invention are as follows:
4-(2-hydroxybenzylideneamino)-3-methylphenol
4-(2-hydroxybenzylideneamino)-3,5-dimethylphenol
4-(2-hydroxy-5-methoxybenzylideneamino)-3,5-dimethylphenol
4-(2-hydroxybenzylideneamino)-3-isopropylphenol
4-(5-bromo-2-hydroxybenzylideneamino)-3-isopropylphenol
4-(3,5-dibromo-2-hydroxybenzylideneamino)-3,5-dimethylphenol
4-(5-chloro-2-hydroxybenzylideneamino)-3,5-dimethylphenol
4-(2-hydroxy-5-nitrobenzylideneamino)-3,5-dimethylphenol
4-(2-hydroxybenzylideneamino)-2-chloro-5-methylphenol
4-(2-hydroxybenzylideneamino)-1-naphthol
4-[1-(2-hydroxyphenyl)ethylideneamino]-3-methylphenol
2,3-dihydro-2,2-dimethyl-4-(2-hydroxybenzylideneamino)benzofuran-7-ol
3-isopropyl-4-(2-hydroxy-1-naphthylmethyleneamino)-phenol Additionally, a preferred imine trisphenol intermediate compound of this invention is 4-(2,4-dihydroxybenzylideneamino)-3,5-dimethylphenol.

Illustrative of the preferred hydroxyarylalkyleneaminoaryl carbamate compounds and derivatives thereof of this invention are as follows:

4-(2-hydroxybenzylideneamino)-3-methylphenyl methylcarbamate 4-(2-hydroxybenzylideneamino)-3,5-dimethylphenyl methylcarbamate 4-(2-hydroxybenzylideneamino)-3-isopropylphenyl methylcarbamate 4-(2-hydroxy-5-methoxybenzylideneamino)-3,5-dimethylphenyl methylcarbamate 4-(5-bromo-2-hydroxybenzylideneamino)-3-isopropylphenyl methylcarbamate 4-(3,5-dibromo-2-hydroxybenzylideneamino)-3,5-dimethylphenyl methylcarbamate 4-(5-chloro-2-hydroxybenzylideneamino)-3,5-dimethylphenyl methylcarbamate 4-(2-hydroxy-5-nitrobenzylideneamino)-3,5-dimethylphenyl methylcarbamate 4-(2-hydroxybenzylideneamino)-2-chloro-5-methylphenyl methylcarbamate 4-(2-hydroxybenzylideneamino)naphth-1-yl methylcarbamate 4-[1-(2-hydroxyphenyl)ethylideneamino]-3-methylphenyl methylcarbamate 2,3-dihydro-2,2-dimethyl-4-(2-hydroxybenzylideneamino)benzofuran-7-yl methylcarbamate 4-[2-hydroxy-4-(methylcarbamoyloxy)benzylideneamino]-3,5-dimethylphenyl methylcarbamate 3-isopropyl-4-(2-hydroxy-1-naphthylmethyleneamino)phenyl methylcarbamate 4-(2-hydroxybenzylideneamino)-3,5-dimethylphenyl methylcarbamate, copper (II) salt di[4-(2-hydroxybenzylideneamino)-3,5-dimethylphenyl]thiobis(methylcarbamate)

di[4-(2-hydroxybenzylideneamino)-3,5-dimethylphenyl]dithiobis(methylcarbamate)

4-(2-hydroxybenzylideneamino)-3,5-dimethylphenyl N-(tert-butylthiosulfenyl)-N-methylcarbamate 4-(2-hydroxybenzylideneamino)-3,5-dimethylphenyl N-(tert-butylphenylsulfenyl)-N-methylcarbamate 4-(2-hydroxybenzylideneamino)-3,5-dimethylphenyl N-(dibutylaminosulfenyl)-N-methylcarbamate 4-(2-hydroxybenzylideneamino)-3-methyl-5-isopropylphenyl methylcarbamate 4-(2-hydroxybenzylideneamino)-3-tert-butylphenyl methylcarbamate 4-(2-hydroxybenzylideneamino)-2,5-dimethylphenyl ethylcarbamate 4-(2-hydroxy-5-methylbenzylideneamino)-3,5-dimethylphenyl methylcarbamate 4-(2-hydroxy-3,5-dimethylbenzylideneamino)-3,5-dimethylphenyl methylcarbamate 4-(2-hydroxybenzylideneamino)-5-methyl-2-methylthiomethylphenyl methylcarbamate 4-[4-(4-chlorophenoxy)-2-hydroxybenzylideneamino]-3-methylphenyl n-propylcarbamate 4-(2-hydroxybenzylideneamino)-2-isopropyl-5-methylphenyl methylcarbamate 4-(5-cyano-2-hydroxybenzylideneamino)-3,5-dimethylphenyl methylcarbamate 4-(2-hydroxy-6-trifluoromethyloxybenzylideneamino)-3,5-dimethylphenyl methylcarbamate 4-(2-hydroxy-6-methylbenzylideneamino)-3-methylnaphth-1-yl methylcarbamate 4-(2-hydroxynaphth-1-ylmethyleneamino)-3-isopropylphenyl methylcarbamate 4-(1-hydroxy-5,6,7,8-tetrahydronaphth-2-ylmethyleneamino)-3,5-dimethylphenyl methylcarbamate The compounds of this invention can be prepared in accordance with a variety of methods. The preferred method for preparing the imine bisphenol intermediate compounds of this invention is illustrated by the general reaction scheme set forth below in which R, $R^1$, $R^2$, $R^3$ and $R^4$ are as described above.

METHOD I

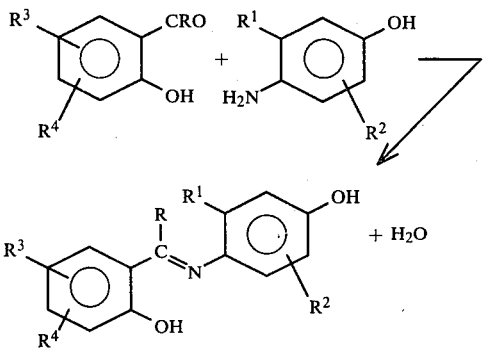

The hydroxyarylalkyleneaminoaryl carbamate compounds and derivatives thereof of this invention can be prepared by a variety of methods as illustrated by the working examples which utilize the imine bisphenol intermediate compounds of this invention as precursors. The preferred method is illustrated by the reaction scheme set forth below in which R, $R^1$, $R^2$, $R^3$, $R^4$, $R^5$ and $R^6$ are as described above.

METHOD II

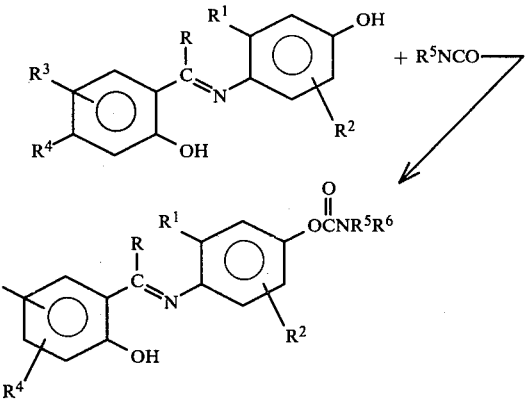

The reactions of Method I and Method II can be conducted in any organic solvent (or mixtures thereof) that is inert to the reactants and reaction conditions. Illustrative of organic solvents that are useful in the conduct of these reactions are saturated, unsaturated and aromatic hydrocarbons such as hexane, cyclohexane, octane, cyclooctane, dodecane, decalin, kerosene, cycloheptane, benzene, toluene, xylene, and the like; ethers such as dioxane, tetrahydrofuran, diethyl ether, tetrahydropyran, 1,2-dimethoxybenzene, dialkyl ethers of ethylene glycol or propylene glycol and the like; chlorinated aliphatic hydrocarbons such as dichloromethane, chloroform, carbon tetrachloride, 1,1-dichloroethane, and the like; or esters such as ethyl acetate and the like. The reaction of Method I can also be conducted in protic solvents such as water, methanol, ethanol, isopropanol, ethylene glycol and the like including mixtures thereof. The preferred solvents for the reactions of Method I and Method II are ethyl acetate, toluene and dichloromethane.

Reaction temperatures are not critical and can be varied over a wide range depending to a large extent on the reactivity and the stability of the reactants. The reaction of Method I is preferably conducted at a temperature of from about 15° C. to about 150° C. The reaction of Method II is preferably conducted at a temperature of from about 0° C. to about 40° C. Reaction pressures are not critical. For convenience these reactions are usually conducted at atmospheric or autogeneous pressure.

The reactions illustrated in Method I and Method II can be conducted in the presence of a quantity of a catalyst sufficient to provide a suitable and reasonable reaction rate. An acid catalyst may be used to effect the reaction of Method I. Illustrative of preferred acids that are useful as a catalyst in this reaction are mineral acids such as hydrochloric acid, sulfuric acid, phosphoric acid and the like. Organic acids are also useful as a catalyst for the reaction of Method I. Suitable organic acids include benzenesulfonic acid, toluenesulfonic acid, acetic acid, propionic acid and the like. In general, any conventional catalyst of the type commonly employed to promote reactions between isocyanate compounds and compounds that contain an active hydrogen can be used (Method II). Illustrative of materials useful as a catalyst in the conduct of the Method II reaction are organic bases such as organic amines, alkali metal alkoxides, alkali metal alkylides and the like and inorganic bases such as alkaline earth hydroxides, alkali metal hydroxides and the like. Organic and inorganic acids may also be used as a catalyst in the reaction of Method II. The preferred catalysts for the reaction of Method II are tertiary amines such as triethylamine, trimethylamine, pyridine, picoline, lutidine, collidine and the like and dibutyltin diacetate.

The hydroxybenzaldehyde compounds utilized as a reactant in the reaction of Method I are commercially available compounds made by known methods. Illustrative of suitable hydroxybenzaldehyde compounds that are useful in the reaction of Method I are salicylaldehyde, 3,6-dimethylsalicylaldehyde, 4-chloro-6-fluorosalicylaldehyde, 6-propylsalicylaldehyde, 5-nitrosalicylaldehyde, 5-methoxysalicylaldehyde, 6-fluorosalicylaldehyde, 6-ethoxysalicylaldehyde, 4,6-dinitrosalicylaldehyde, 3,5-dimethoxysalicylaldehyde, 4,6-dichlorosalicylaldehyde, 6-chlorosalicylaldehyde, 4-bromosalicylaldehyde and the like. The preferred hydroxybenzaldehyde compound useful as a reactant in the reaction of Method I is salicylaldehyde. Additionally, ketone compounds may be used as a reactant in the reaction of Method I. The preferred ketone compound for use in this reaction is 2-hydroxyacetophenone.

The aminophenol compounds utilized as a reactant in the reaction of Method I are commercially available compounds made by known methods. Illustrative of suitable aminophenol compounds that are useful in the reaction of Method I are 4-amino-3-methylphenol, 4-amino-3,5-dimethylphenol, 4-aminophenol, 4-amino-3-chlorophenol, 4-amino-3,5-diethylphenol, 4-amino-3-fluorophenol and the like. The preferred aminophenol compounds useful as reactants in the reaction of Method I are 4-amino-3-methylphenol and 4-amino-3,5-dimethylphenol.

The isocyanate compounds utilized as a reactant in the reaction of Method II are commercially available compounds made by known methods. Illustrative of suitable isocyante compounds that are useful in the reaction of Method II are methyl isocyanate, ethyl isocyanate, propyl isocyanate and the like. The preferred isocyanate compound useful as a reactant in the reaction of Method II is methyl isocyanate.

The reaction of Method I is preferably carried out by reacting essentially equimolar proportions of the appropriate hydroxybenzaldehyde compound with the appropriate aminophenol compound. The reaction is usually but not necessarily carried out in the presence of a solvent which is inert to the reactants and reaction conditions. An acid catalyst may or may not be used to effect the reaction of Method I. The reaction of Method I is conducted over a period of time of from about one hour to about 48 hours at a temperature range of from about 15° C. to 150° C. One method of carrying out this reaction requires heating the appropriate hydroxybenzaldehyde compound and aminophenol compound in a solvent inert to the reactants and reaction conditions for a period of from six to 24 hours. Another method of carrying out this reaction requires heating the appropriate hydroxybenzaldehyde compound and aminophenol compound in a solvent inert to the reactants and reaction conditions and azeotropically removing water as a product of the reaction with a high-boiling solvent. Isolation of the desired imine bisphenol intermediate compound may be carried out by several methods common in the art. The preferred reaction conditions for effecting the preparation of imine bisphenol intermediate compounds are dependent on the hydroxybenzaldehyde compound and aminophenol compound utilized in the reaction.

The reaction of Method II is preferably carried out by reacting one equivalent or more of an isocyanate compound with the imine bisphenol intermediate compound prepared in Method I. The reaction is preferably conducted in the presence of a solvent inert to the reactants and reaction conditions and also in the presence of a catalyst. The reaction of Method II is conducted over a period of time of from about one hour to about 48 hours at a temperature range of from about 0° C. to 40° C. The desired hydroxyarylalkyleneaminoaryl carbamate compound can be isolated by one of many methods common in the art.

Tautomerism must be considered in regard to the true structure of the compounds of this invention. It should be clear to anyone skilled in the art that the hydroxyarylalkyleneamino portion of the compounds of this invention can be represented as a tautomeric modification illustrated below:

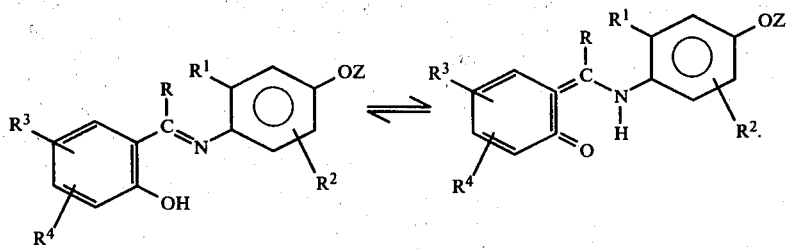

This tautomeric modification can occur when the compounds of this invention are in solution. However, it should be noted that the compounds of this invention as structurally depicted above greatly predominate in a solution containing both these compounds and the tautomeric modified compounds thereof.

The compounds contemplated in this invention may be applied as insecticides according to methods known to those skilled in the art. Insecticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

Spray adjuvants such as Coax ® and Gustol ® have been developed for enhancing the effectiveness of biological insecticides. Coax ® and Gustol ® are cotton extracts which generally enhance feeding by insects. When these products are co-applied with insecticides, the increased consumption by the insects of treated foliage results in improved performance relative to the toxicants applied alone. When 4-(2-hydroxybenzylideneamino)-3,5-dimethylphenyl methylcarbamate of this invention was mixed with Coax ® and Gustol ® respectively and co-applied with bean plants infested with southern armyworm, tobacco budworm and cotton bollworm, an improvement in the toxicity of 4-(2-hydroxybenzylideneamino)-3,5-dimethylphenyl methylcarbamate alone with respect to these particular pests was demonstrated.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The insecticides contemplated herein prevent attack by insects upon plants or other material to which the insecticides are applied. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable insecticidal characteristic of the toxicants or impart undesirable characteristics, for instance, phytotoxicity, to the toxicants. The toxicants are compatible with other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds.

The following examples are illustrative of the present invention and are not intended as a limitation upon the scope thereof.

EXAMPLE I

Part A: Preparation of
4-(2-Hydroxybenzylideneamino)-3-methylphenol
Intermediate To a 500 milliliter round bottom flask equipped with a water condenser, magnetic stirrer and drying tube was added 12.32 grams (0.10 mole) of 4-amino-3-methylphenol, 12.21 grams (0.10 mole) of salicylaldehyde and 250 milliliters of ethyl acetate. The resulting reaction mixture was stirred for 19 hours at room temperature and ambient pressure. After the stirring period, the reaction mixture was washed twice with saturated brine solution and decolorized with activated charcoal. The reaction mixture was then dried over magnesium sulfate, filtered and concentrated under reduced pressure to give a yellow oil which solidified on standing. The resulting solidified material was slurried in hexane, collected by filtration and dried to yield 21.12 grams (0.093 moles) of 4-(2-hydroxybenzylideneamino)-3-methylphenol in the form of a yellow solid having a melting point of 95°–97° C.

Calculated for $C_{14}H_{13}NO_2$ (weight percent): C, 73.98; H, 5.78; N, 6.16; Found (weight percent): C, 72.77; H, 6.12; N, 6.32.

Part B: Preparation of
4-(2-Hydroxybenzylideneamino)-3-methylphenyl Methylcarbamate To a 350 milliliter glass pressure bottle equipped with a magnetic stirrer was added 4.54 grams (0.020 moles) of 4-(2-hydroxybenzylideneamino)-3-methylphenol prepared in Part A, 2.57 grams (0.045 moles) of methyl isocyanate, 100 milliliters of ethyl acetate and 5 drops of dibutyltin diacetate. The resulting reaction mixture was stirred for 24 hours at room temperature forming a precipitate. The precipitate was removed from the reaction mixture by filtration, washed with cold hexane and air dried to give 5.69 grams (0.020 moles) of 4-(2-hydroxybenzylideneamino)-3-methylphenyl methylcarbamate in the form of a yellow solid having a melting point of 156.5°–157° C. and the following structural formula:

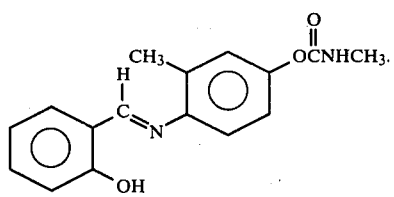

Calculated for $C_{16}H_{16}N_2O_3$ (weight percent): C, 67.59; H, 5.68; N, 9.85; Found (weight percent): C, 67.86; H, 5.77; N, 9.89.

EXAMPLE II

Part A: Preparation of
4-(2-Hydroxybenzylideneamino)-3,5-dimethylphenol Intermediate To a 500 milliliter round bottom flask equipped with a water condenser, magnetic stirrer and drying tube was added 13.72 grams (0.10 mole) of 4-amino-3,5-dimethylphenol, 12.21 grams (0.10 mole) of salicylaldehyde and 250 milliliters of ethyl acetate. The resulting reaction mixture was then heated to 55° C. and stirred for 19 hours at ambient pressure. After cooling the reaction mixture to room temperature, it was filtered and concentrated under reduced pressure to give a brown oil which solidified on standing. The resulting solidified material was slurried in hexane, collected by filtration and dried to yield 19.66 grams (0.082 moles) of 4-(2-hydroxybenzylideneamino)-3,5-dimethylphenol in the form of a yellow solid having a melting point of 145°–147° C.

Calculated for $C_{15}H_{15}NO_2$ (weight percent): C,74.66; H, 6.30; N, 5.80; Found (weight percent): C, 73.60; H, 6.18; N, 5.65.

Part B: Preparation of
4-(2-Hydroxybenzylideneamino)-3,5-dimethylphenyl Methylcarbanate To a 350 milliliter glass pressure bottle equipped with a magnetic stirrer was added 6.03 grams (0.025 moles) of 4-(2-hydroxybenzylideneamino)-3,5-dimethylphenol prepared in Part A, 1.71 grams (0.030 moles) of methyl isocyanate, 50 milliliters of ethyl acetate and 5 drops of dibutyltin diacetate. The resulting reaction mixture was stirred for 65 hours at room temperature and then washed twice with a 1% aqueous sodium bicarbonate solution followed by a single wash with saturated brine solution. After drying the reaction mixture over magnesium sulfate, it was collected by filtration and concentrated under reduced pressure to give a brown oil. The oil was triturated with hexane to give 5.21 grams (0.017 moles) of 4-(2-hydroxybenzylideneamino)-3,5-dimethylphenyl methylcarbamate in the form of a yellow solid having a melting point of 116°–118° C. and the following structural formula:

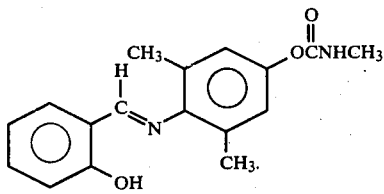

Calculated for $C_{17}H_{18}N_2O_3$ (weight percent): C, 68.44; H, 6.09; N, 9.38; Found (weight percent): C, 67.06; H, 6.05; N, 9.36.

EXAMPLE III

In a manner similar to that described in Example II, 4-(2-hydroxy-5-methoxybenzylideneamino)-3,5-dimethylphenyl methylcarbamate was prepared having a melting point of 125°–129° C. and the following structural formula:

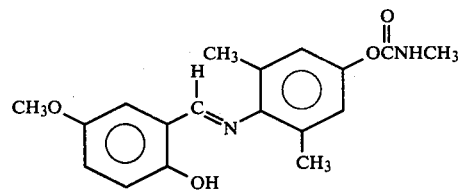

Calculated for $C_{18}H_{20}N_2O_4$ (weight percent): C, 65.84; H, 6.15; N, 8.53; Found (weight percent): C, 63.48; H, 6.09; N, 8.90.

EXAMPLE IV

In a manner similar to that described in Example II, 4-(2-hydroxybenzylideneamino)-3-isopropylphenyl methylcarbamate was prepared having a melting point of 158°–159° C. and the following structural formula:

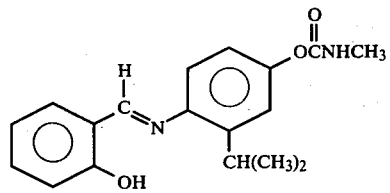

Calculated for $C_{18}H_{20}N_2O_3$ (weight percent): C,69.21; H,6.47; N,8.97; Found (weight perecent): C,69.50; H,6.39; N,9.02.

EXAMPLE V

In a manner similar to that described in Example II, 4-(5-bromo-2-hydroxybenzylideneamino)-3-isopropylphenyl methylcarbamate was prepared having a melting point of 164°–165° C. and the following structural formula:

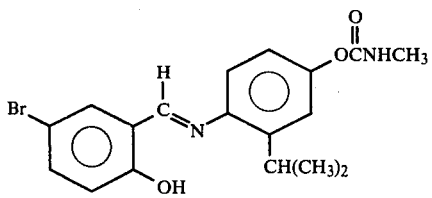

Calculated for $C_{18}H_{19}BrN_2O_3$ (weight percent): C,55.25; H,4.90; N,7.16; Found (weight percent): C,55.06; H,4.70; N,7.23.

EXAMPLE VI

In a manner similar to that described in Example II, 4-(3,5-dibromo-2-hydroxybenzylideneamino)-3,5-dimethylphenyl methylcarbamate was prepared having a melting point of 203°–207° C. and the following structural formula:

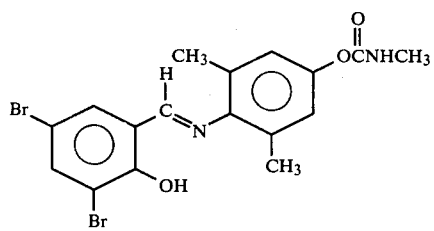

Calculated for $C_{17}H_{16}Br_2N_2O_3$ (weight percent): C,44.76; H,3.54; N,6.14; Found (weight percent): C,44.90; H,3.60; N,6.39.

EXAMPLE VII

In a manner similar to that described in Example II, 4-(5-chloro-2-hydroxybenzylideneamino)-3,5-dimethylphenyl methylcarbamate was prepared having a melting point of 151°–155° C. and the following structural formula:

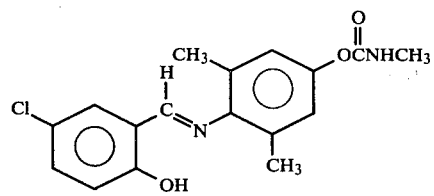

Calculated for $C_{17}H_{17}ClN_2O_3$ (weight percent): C,61.35; H,5.16; N,8.42; Found (weight percent): C,60.31; H,5.12; N,8.44.

EXAMPLE VIII

In a manner similar to that described in Example II, 4-(2-hydroxy-5-nitrobenzylideneamino)-3,5-dimethylphenyl methylcarbamate was prepared having a melting point of 195°–215° C. and the following structural formula:

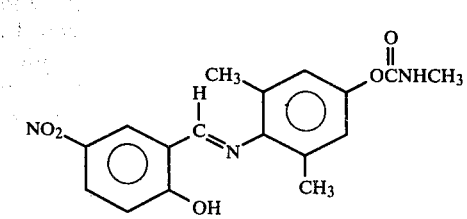

Calculated for $C_{17}H_{17}N_3O_5$ (weight percent): C,59.45; H,5.00; N,12.24; Found (weight percent): C,59.49; H,5.09; N,11.70.

EXAMPLE IX

In a manner similar to that described in Example II, 4-(2-hydroxybenzylideneamino)-2-chloro-5-methylphenyl methylcarbamate was prepared having a melting point of 148°–151.5° C. and the following structural formula:

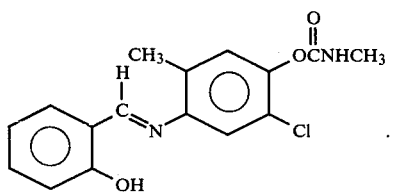

Calculated for $C_{16}H_{15}ClN_2O_3$ (weight percent): C,60.25; H,4.75; N,8.79; Found (weight percent): C,59.17; H,4.85; N,8.15.

EXAMPLE X

Part A: Preparation of
4-(2-Hydroxybenzylideneamino)-1-naphthol
Intermediate

To a 500 milliliter round bottom flask equipped with a water condenser, magnetic stirrer and drying tube was added 5.50 grams (0.045 moles) of salicylaldehyde, 4.10 grams (0.050 moles) of sodium acetate and 40 milliliters of ethanol. The resulting mixture was then heated to a temperature of 50° C. and a solution consisting of 7.83 grams (0.040 moles) of 4-amino-1-naphthol hydrochloride in 20 milliliters of water was added thereto. The resulting reaction mixture was stirred for 15 minutes at a temperature of 50° C. and then cooled to room temperature forming a precipitate. The precipitate was removed from the reaction mixture by filtration, washed with water and dried over magnesium sulfate to give 8.68 grams (0.033 moles) of 4-(2-hydroxybenzylideneamino)-1-naphthol in the form of reddish-brown crystals having a melting point of 153.5°–157° C.

Calculated for $C_{17}H_{13}NO_2$ (weight percent): C,77.54; H,4.99; N,5.32; Found (weight percent): C,77.08; H,4.94; N, 5.22.

Part B: Preparation of
4-(2-Hydroxybenzylideneamino)naphth-1-yl
Methylcarbamate

To a 350 milliliter glass pressure bottle equipped with a magnetic stirrer was added 4.00 grams (0.015 moles) of 4-(2-hydroxybenzylideneamino)-1-naphthol prepared in Part A, 1.03 grams (0.018 moles) of methyl isocyanate, 100 milliliters of tetrahydrofuran and 5 drops of dibutyl tin diacetate. The resulting reaction mixture was stirred for 18 hours at room temperature after which the volatiles were removed under reduced pressure and the remaining residue dissolved in ether. The ethereal solution was washed twice with a 1% aqueous sodium bicarbonate solution and twice with a saturated brine solution, dried over magnesium sulfate and concentrated under reduced pressure to give 4.87 grams (0.015 moles) of 4-(2-hydroxybenzylideneamino)naphth-1-yl methylcarbamate in the form of a pale yellow solid having a melting point of 143°–145.5° C. and the following structural formula:

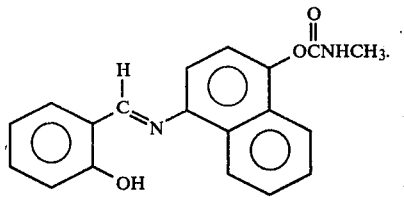

Calculated for $C_{19}H_{16}N_2O_3$ (weight percent): C,71.23; H,5.04; N,8.75; Found (weight percent): C,69.85; H,5.03; N,8.94.

EXAMPLE XI

Part A: Preparation of 4-[1-(2-Hydroxyphenyl)ethylideneamino]-3-methylphenol Intermediate To a 1 liter round bottom flask equipped with a water collector, water condenser, magnetic stirrer and drying tube was added 12.32 grams (0.10 mole) of 4-amino-3-methylphenol, 14.30 grams (0.105 mole) of 2-hydroxyacetophenone, 0.6 grams (0.005 moles) of p-toluenesulfonic acid and 500 milliliters of toluene. The resulting reaction mixture was stirred and refluxed for 100 hours during which time water was collected from the reaction. After the stirring and refluxing period, the reaction mixture was cooled to room temperature, filtered and left standing for 50 hours forming a solid material. The resulting solidified material was removed by filtration and recrystallized from toluene to give 10.10 grams (0.042 moles) of 4-[1-(2-hydroxyphenyl)ethylideneamino]-3-methylphenol having a melting point of 144°–156° C.

Calculated for $C_{15}H_{15}NO_2$ (weight percent): C,74.66; H,6.28; N,5.81; Found (weight percent): C,74.17; H,6.37; N,6.19.

Part B: Preparation of 4-[1-(2-Hydroxyphenyl)ethylideneamino]-3-methylphenyl Methylcarbamate To a 350 milliliter glass pressure bottle equipped with a magnetic stirrer was added 4.83 grams (0.020 moles) of 4-[1-(2-hydroxyphenyl)ethylideneamino]-3-methylphenol prepared in Part A, 1.42 grams (0.025 moles) of methyl isocyanate, 100 milliliters of ethyl acetate and 5 drops of dibutyl tin diacetate. The resulting reaction mixture was stirred for 96 hours at room temperature, filtered and then washed twice with a 1% aqueous sodium bicarbonate solution followed by a single wash with saturated brine solution. After drying the reaction mixture over magnesium sulfate, it was concentrated under reduced pressure to give 5.36 grams (0.018 moles) of 4-[1-(2-hydroxyphenyl)ethylideneamino]-3-methylphenyl methylcarbamate in the form of an orange solid having a melting point of 133°–138° C. and the following structural formula:

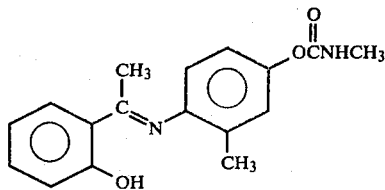

Calculated for $C_{17}H_{18}N_2O_3$ (weight percent): C,68.44; H,6.09; N,9.39, Found (weight percent): C,67.54; H,6.03; N,9.47.

EXAMPLE XII

Part A: Preparation of 2,3-Dihydro-2,2-dimethyl-4-(2-hydroxybenzylideneamino)benzofuran-7-ol Intermediate To a 500 milliliter round bottom flask equipped with a water collector, water condenser, magnetic stirrer and drying tube was added 5.38 grams (0.030 moles) of 4-amino-2,3-dihydro-2,2-dimethyl-7-hydroxybenzofuran, 3.91 grams (0.032 moles) of salicylaldehyde and 300 milliliters of ethyl acetate. The resulting reaction mixture was heated to reflux with removal of the first 50 milliliters of distillate, and the remaining mixture allowed to reflux for 1 additional hour with continuous stirring. After the stirring and refluxing period, the reaction mixture was cooled to room temperature, filtered, dried over magnesium sulfate and concentrated under reduced pressure to give 6.15 grams (0.022 moles) of 2,3-dihydro-2,2-dimethyl-4-(2-hydroxybenzylideneamino)benzofuran-7-ol in the form of a dark red oil.

Part B: Preparation of 2,3-Dihydro-2,2-dimethyl-4-(2-hydroxybenzylideneamino)benzofuran-7-yl Methylcarbamate To a 350 milliliter glass pressure bottle equipped with a magnetic stirrer was added 6.00 grams (0.021 moles) of 2,3-dihydro-2,2-dimethyl-4-(2-hydroxybenzylideneamino)benzofuran-7-ol prepared in part A, 1.4 grams (0.024 moles) of methyl isocyanate, 100 milliliters of methylene chloride and 0.1 milliliters of triethylamine. The resulting reaction mixture was stirred for 66 hours at room temperature and then concentrated under reduced pressure to give a yellow solid material. The yellow solid material was washed with hexane and dried to yield 6.64 grams (0.0195 moles) of 2,3-dihydro-2,2-dimethyl-4-(2-hydroxybenzylideneamino)benzofuran-7-yl methylcarbamate in the form of a yellow solid having a melting point of 201°–203° C. and the following structural formula:

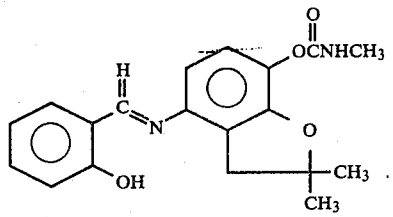

Calculated for $C_{19}H_{20}N_2O_4$ (weight percent): C,67.04; H,5.93; N, 8.23; Found (weight percent): C,66.55; H,5.90; N,8.16.

EXAMPLE XIII

Part A: Preparation of 4-(2,4-Dihydroxybenzylideneamino)-3,5-dimethylphenol Intermediate In a manner similar to that described in Example XII, Part A, 4-(2,4-dihydroxybenzylideneamino)-3,5-dimethylphenol was prepared from 2,4-dihydroxybenzaldehyde and 4-amino-3,5-dimethylphenol forming a yellow solid and having a melting point of 193°–197° C.

Calculated for $C_{15}H_{15}NO_3$ (weight percent): C,70.02; H,5.89; N,5.44; Found (weight percent): C,68.72; H, 5.86; N,5.12.

Part B: Preparation of 4-[2-Hydroxy-4-(methylcarbamoyloxy)benzylideneamino]-3,5-dimethylphenyl Methylcarbamate To a 350 milliliter glass pressure bottle equipped with a magnetic stirrer was added 5.15 grams (0.020 moles) of 4-(2,4-dihydroxybenzylideneamino)-3,5-dimethylphenol prepared in Part A, 2.40 grams (0.042 moles) of methyl isocyanate, 100 milliliters of ethyl acetate and 5 drops of dibutyltin diacetate. The resulting reaction mixture was stirred for 18 hours at room temperature, diluted with an additional 100 milliliters of ethyl acetate and washed twice with a 1% aqueous sodium bicarbonate solution followed by a single wash with saturated brine solution. After drying the reaction mixture over magnesium sulfate, it was concentrated under reduced pressure to give 7.25 grams (0.0195 moles) of 4-[2-hydroxy-4-(methylcarbamoyloxy)benzylideneamino]-3,5-dimethylphenyl methylcarbamate in the form of a yellow solid having a melting point of 70°–65° C. and the following structural formula:

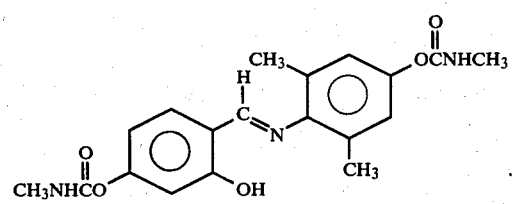

Calculated for $C_{19}H_{21}N_3O_5$ (weight percent): C,61.44; H,5.70; N,11.31; Found (weight percent): C,61.34; H,5.94; N,11.00.

EXAMPLE XIV

In a manner similar to that described in Example XII, 3-isopropyl-4-(2-hydroxy-1-naphthylmethyleneamino)phenyl methylcarbamate was prepared having a melting point of 168°–182° C. and the following structural formula:

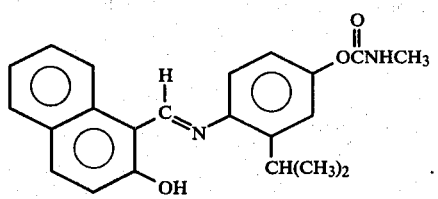

Calculated for $C_{22}H_{22}N_2O_3$ (weight percent): C,72.90; H,6.13; N,7.73; Found (weight percent): C,72.71; H,6.08; N,7.51.

EXAMPLE XV

In a manner identical to that described in Example II, 4-(2-hydroxybenzylideneamino)-3,5-dimethylphenyl methylcarbamate was prepared. To a 300 milliliter round bottom flask was added 2.98 grams (0.010 moles) of 4-(2-hydroxybenzylideneamino)-3,5-dimethylphenyl methylcarbamate, 2.00 grams (0.010 moles) of copper (II) acetate monohydrate and 100 milliliters of methanol. The resulting reaction mixture was heated to reflux for 15 minutes with continuous stirring. After the stirring and refluxing period, the reaction mixture was cooled to room temperature, filtered and dried over magnesium sulfate for 24 hours to give 2.45 grams (0.0037 moles) 4-(2-hydroxybenzylideneamino)-3,5-dimethylphenyl methylcarbamate, copper (II) salt in the form of a brown solid having a melting point of 229°–231° C. (decomposition) and the following structural formula:

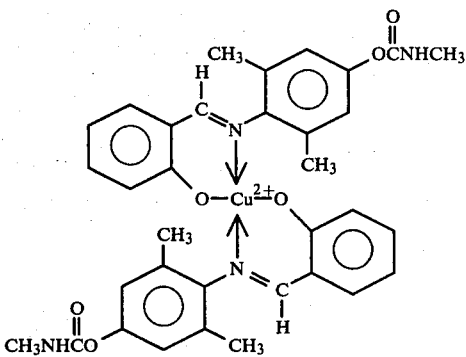

Calculated for $C_{34}H_{34}CuN_4O_6$ (weight percent): C,62.04; H,5.22; N,8.51; Found (weight percent): C,61.88; H,5.38; N,8.45.

EXAMPLE XVI

In a manner identical to that described in Example II, Part A, 4-(2-hydroxybenzylideneamino)-3,5-dimethylphenol was prepared. To a 300 milliliter round bottom flask equipped with a water condenser, magnetic stirrer and drying tube was added 4.34 grams (0.018 moles) of 4-(2-hydroxybenzylideneamino)-3,5-dimethylphenol, 2.02 grams (0.020 moles) of triethylamine, 1.65 grams (0.009 moles) of bis-(N-methyl-N-fluorocarbonylamino) sulfide and 150 milliliters of ethyl acetate. The resulting reaction mixture was heated to reflux for 18 hours with continuous stirring. After the stirring and refluxing period, the reaction mixture was cooled to room temperature and washed three times with water and twice with a saturated brine solution. The reaction mixture was then dried over magnesium sulfate and concentrated under reduced pressure to give 5.60 grams of (0.0089 moles) of di[4-(2-hydroxybenzylideneamino)-3,5-dimethylphenyl]thiobis(methylcarbamate) in the form of an orange solid having a melting point of 93°–110° C. and the following structural formula:

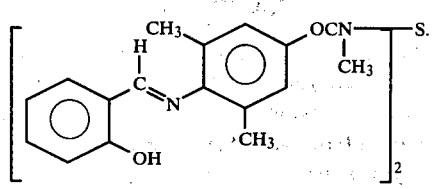

Calculated for C34H34N4O6S (weight percent): C,65.16; H,5.48; N,8.94; Found (weight percent): C,64.01; H,5.62; N,8.34.

EXAMPLE XVII

In a manner similar to that described in Example XVI, di[4-(2-hydroxybenzylideneamino)-3,5-dimethylphenyl]dithiobis(methylcarbamate) was prepared having a melting point of 185°–186° C. and the following structural formula:

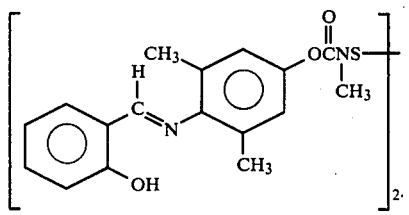

Calculated for C34H34N4O6S2 (weight percent): C,61.98; H,5.21; N,8.51; Found (weight percent): C,61.90; H,5.16; N,8.51.

EXAMPLE XVIII

In a manner identical to that described in Example II, Part A, 4-(2-hydroxybenzylideneamino)-3,5-dimethylphenol was prepared. To a 500 milliliter round bottom flask equipped with a water condenser, magnetic stirrer and drying tube was added 4.83 grams (0.020 moles) of 4-(2-hydroxybenzylideneamino)-3,5-dimethylphenol, 3.95 grams (0.020 moles) of N-(tertbutylthiosulfenyl)-N-fluorocarbonyl-N-methylamine, 2.12 grams (0.021 moles) of triethylamine and 200 milliliters of toluene. The resulting reaction mixture was heated to a temperature of 50° C. in an oil batch for 16 hours with continuous stirring. After this heating and stirring period, 1.0 grams (0.0041 moles) of N-tert-butylthiosulfenyl)-N-fluorocarbonyl-N-methylamine and 0.5 grams (0.005 moles) of triethylamine were added to the reaction mixture and heating continued for an additional 3 hours at a temperature of 50° C. with continuous stirring. The reaction mixture was cooled to room temperature and then washed twice with water, twice with a 2% aqueous sodium bicarbonate solution and once with a saturated brine solution. After drying the reaction mixture over magnesium sulfate, it was concentrated under reduced pressure to give a red oil. Purification of the red oil by column chromatography yielded 2.02 grams (0.0048 moles) of 4-(2-hydroxybenzylideneamino)-3,5-dimethylphenyl N-(tert-butylthiosulfenyl)-N-methylcarbamate in the form of a yellow solid having a melting point of 121°–124° C. and the following structural formula:

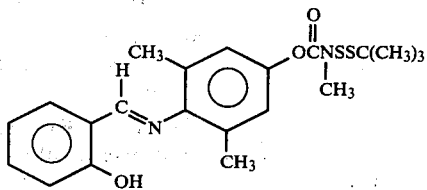

Calculated for C21H26N2O3S2 (weight percent): C,60.25; H,6.27; N,6.69; Found (weight percent): C,60.18; H,6.28; N,6.66.

EXAMPLE XIX

In a manner similar to that described in Example XVIII, 4-(2-hydroxybenzylideneamino)-3,5-dimethylphenyl N-(4-tert-butylphenylsulfenyl)-N-methylcarbamate was prepared having a melting point of 60°–63° C. and the following structural formula:

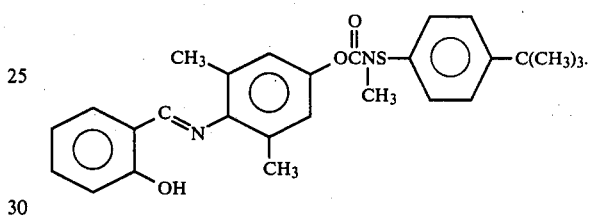

Calculated for C27H30N2O3S (weight percent): C,70.09; H,6.55; N,6.06; Found (weight percent): C,69.61; H,6.63; N,6.01.

EXAMPLE XX

In a manner identical to that described in Example II, Part A, 4-(2-hydroxybenzylideneamino)-3,5-dimethylphenol was prepared. To a 1 liter round bottom flask equipped with a magnetic stirrer was added 9.65 grams (0.040 moles) of 4-(2-hydroxybenzylideneamino)-3,5-dimethylphenol, 10.65 grams (0.045 moles) of N-(di-n-butylaminosulfenyl)-N-fluorocarbonyl-N-methylamine, 400 milliliters of toluene, 100 milliliters of 0.4 molar sodium hydroxide and 10 drops of tricaprylmethylammonium chloride solution. The resulting reaction mixture was stirred continuously for 2 hours at room temperature forming an organic layer. After the stirring period, the organic layer was separated, washed twice with water and twice with a saturated brine solution, dried over magnesium sulfate and concentrated under reduced pressure to give a dark brown oil. Purification of the dark brown oil by column chromatography yielded 2.80 grams (0.0061 moles) of 4-(2-hydroxybenzylideneamino)-3,5-dimethylphenyl N-(dibutylaminosulfenyl)-N-methylcarbamate in the form of an amber oil having the following structural formula:

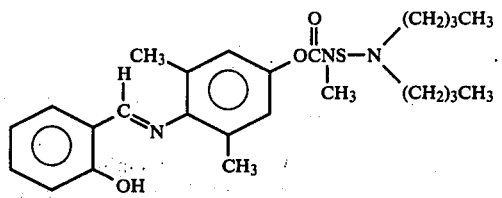

Calculated for C$_{25}$H$_{35}$N$_3$O$_3$S (weight percent): C,65.61; H,7.72; N,9.18; Found (weight percent): C,64.81; H,8.08; N,9.33.

For the purpose of comparison, the following compounds outside the scope of this invention and within the scope of U.S. Pat. No. 3,012,068 were prepared in accordance with the teachings of U.S. Pat. No. 3,012,068:

EXAMPLE A 4-(2,4-Dichlorobenzylideneamino)-3,5-dimethylphenyl Methylcarbamate

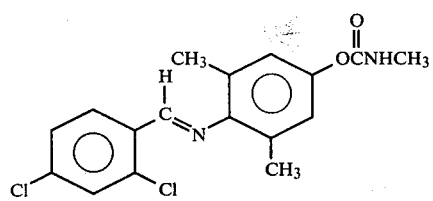

Calculated for C$_{17}$H$_{16}$N$_2$O$_2$Cl$_2$ (weight percent): C,58.13; H,4.60; N,7.97; Found (weight percent): C,57.86; H,4.67; N,7.84.

EXAMPLE B 4-(4-Dimethylaminobenzylideneamino)-3,5-dimethylphenyl Methylcarbamate

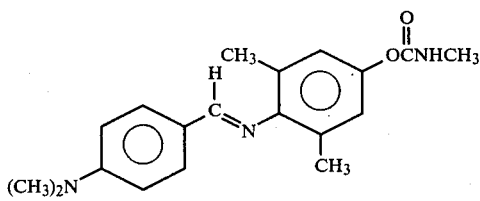

Calculated for C$_{19}$H$_{23}$N$_3$O$_2$ (weight percent): C,70.12; H,7.14; N,12.92; Found (weight percent): C,66.66; H,6.85; N,12.90.

EXAMPLE C

4-Benzylideneamino-3,5-dimethylphenyl Methylcarbamate

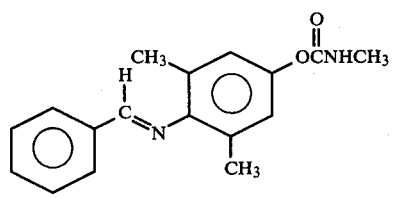

Calculated for C$_{17}$H$_{18}$N$_2$O$_2$ (weight percent): C,72.31; H,6.44; N,9.92; Found (weight percent): C,72.65; H,6.60; N,9.34.

EXAMPLE D 4-(2-Methoxybenzylideneamino)-3,5-dimethylphenyl Methylcarbamate

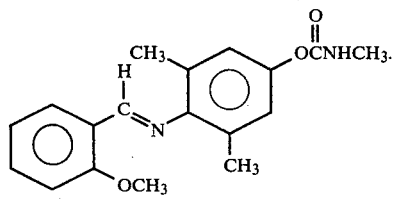

Calculated for C$_{18}$H$_{20}$N$_2$O$_3$ (weight percent): C,69.21; H,6.45; N,8.97; Found (weight percent): C,69.54; H,6.71; N,8.00.

EXAMPLES XXI through XLII

The novel compounds of this invention and the comparative compounds within the scope of U.S. Pat. No. 3,012,068 were evaluated with respect to their activity against representative insects including an aphid, a caterpillar and a beetle.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight (ppm) employed in the tests described hereinbelow were obtained by appropriate dilutions of the stock suspension with water. The test procedures were as follows:

Bean Aphid Local Systemic Test

Adults and nymphal stages of the bean aphid (*Aphis fabae Scop.*) reared on potted dwarf nasturtium plants at 68°-70° F. and 50±5 percent relative humidity, constituted the test insects. The height of the test plants was 5-8 inches. Two leaves, each of which was infested with approximately 50 aphids on the undersurface, were selected. The leaf blade should be fully expanded to 1-1½ inches in diameter.

The test compounds were formulated by diluting the stock suspension with water to give a series of concentrations for determining the LD$_{50}$ value.

Two infested leaves per pot were selected for each concentration. All excess plants and leaves were trimmed away and any aphids remaining on the stem were removed. Leaves from two different plants or from the same plant may be used and each stem was staked and tied separately. Tanglefoot ® was spread with a metal probe on the edge of the upper surface of each leaf and around the base of the petiole. The aqueous preparation of test compound was applied with a small paintbrush to the upper surface of the leaves and during this process all aphids on this surface were removed. The treatment should be confined only to the surface inside the Tanglefoot ® ring. During the painting of the leaves, excess chemical is absorbed with paper towels. As a control, infested leaves were treated with a water-acetone-emulsifier solution containing no test compound in the same concentration as the insecticidal mixture. The treated pots were then placed on their sides on a sheet of white standard mimeograph paper which had been previously ruled into squares to facilitate counting. Temperature and relative humidity in the test room during the 24-hour holding period were maintained at 68°–70° F. and 50±5 percent respectively. After the holding period, the number of dead or living aphids were counted. Aphids which fell onto the paper and were unable to stand after being uprighted were considered dead. Aphids remaining on the underside of the leaves were observed closely for movement and those which were unable to move the length of the body even upon stimulation by prodding were considered dead. Percent mortality was recorded for various concentration levels.

Bean Aphid General Systemic Test

Adults and nymphal stages of the bead aphid (*Aphis fabae Scop.*) reared on potted dwarf nasturtium plants at 68°–70° F. and 50±5 percent relative humidity, constituted the test insects. The height of the test plants was 5–8 inches. For testing purposes, the number of aphids per plant were standardized to 100–150 aphids by trimming plants containing excess aphids.

The test compounds were formulated by diluting the stock suspension with water to give a series of concentrations for determining the $LD_{50}$ value.

The infested plants and their roots were carefully removed from the soil and any loose soil was shaken off. One plant was used for each concentration being tested. The root system was transferred to an Erlenmeyer flask that contained 50 milliliters of the aqueous preparation of test compound. As a control, the root systems of infested plants were treated with a water-acetate-emulsifier solution containing no test compound in the same concentration as the insecticidal mixture. The treated flasks were placed on their sides on a sheet of white standard mimeograph paper which had been previously ruled into squares to facilitate counting. Temperature and relative humidity in the test room during the 24-hour holding period were maintained at 68°–70° F. and 50±5 percent respectively. After the holding period, the number of dead or living aphids were counted. Aphids which fell onto the paper and were unable to stand after being uprighted were considered dead. Aphids remaining on the plants were observed closely for movement and those which were unable to move the length of the body even upon stimulation by prodding were considered dead. Percent mortality was recorded for various concentration levels.

Bean Aphid Foliage Spray Test

Adults and nymphal stages of the bean aphid (*Aphis fabae Scop.*) reared on potted dward nasturtium plants at 68°–70° F. and 50±5 percent relative humidity, constituted the test insects. For testing purposes, the number of aphids per pot were standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Spodoptera eridania*, (*Cram.*)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, *Muls.*), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F., for three days. Although the larvae could easily consume the leaf within 24 to 48 hours, no more food was added. Larvae which were unable to move the length of the body, even upon stimulation, were considered dead. Percent mortality was recorded for various concentration levels.

The results of these tests are set forth in Tables I through IV below. It should be understood that the insects evaluated are representative of a wider variety of pest which can be controlled by the compounds of this invention.

The results of examples in which 4-(2-hydroxybenzylideneamino)-3,5-dimethylphenyl methylcarbamate and the comparative compounds within the scope of U.S. Pat. No. 3,012,068 were tested for local systemic activity against the bean aphid are given below in Table I. The results are rated as a $LD_{50}$ value in ppm (parts of test compound per million parts of final formulation required to achieve a mortality rate of 50 percent).

TABLE I

LOCAL SYSTEMIC ACTIVITY AGAINST THE BEAN APHID (BEAN APHID LOCAL SYSTEMIC TEST)

| Example | Compound | $LD_{50}$(ppm) |
|---|---|---|
| XXI | 4-(2-hydroxybenzylideneamino)-3,5-dimethylphenyl methylcarbamate | 4.5 |
| E | 4-(2,4-dichlorobenzylideneamino)-3,5-dimethylphenyl methylcarbamate | >31 |
| F | 4-benzylideneamino-3,5-dimethylphenyl methylcarbamate | 20 |
| G | 4-(4-dimethylaminobenzylideneamino)-3,5-dimethylphenyl methylcarbamate | 15 |
| H | 4-(2-methoxybenzylideneamino)-3,5-dimethylphenyl methylcarbamate | 15 |

The results of Table I clearly demonstrate the superior local systemic activity against bean aphids of 4-(2-hydroxybenzylideneamino)-3,5-dimethylphenyl methylcarbamate in comparison with the compounds within the scope of U.S. Pat. No. 3,012,068. 4-(2-Hydroxybenzylideneamino)-3,5-dimethylphenyl methylcarbamate exhibited a greater than seven-fold increase in local systemic activity against the bead aphid in comparison with 4-(2,4-dichlorobenzylideneamino)-3,5-dimethylphenyl methylcarbamate, a greater than four-fold increase in local systemic activity against the bean aphid in comparison with 4-benzylideneamino-3,5-dimethylphenyl methylcarbamate and a greater than three-fold increase in local systemic activity against the bean aphid in comparison with both 4-(4-dimethylaminobenzylideneamino-3,5-dimethylphenyl methylcarbamate and 4-(2-methoxybenzylideneamino)-3,5-dimethylphenyl methylcarbamate.

The results of examples in which 4-(2-hydroxybenzylideneamino)-3,5-dimethylphenyl methylcarbamate and the comparative compounds within the scope of U.S. Pat. No. 3,012,068 were tested for general systemic activity against the bean aphid are given below in Table II. The results are rated as a $LD_{50}$ value in ppm.

TABLE II

GENERAL SYSTEMIC ACTIVITY AGAINST THE BEAN APHID (BEAN APHID GENERAL SYSTEMIC TEST)

| Example | Compound | $LD_{50}$(ppm) |
|---|---|---|
| XXII | 4-(2-hydroxybenzylideneamino)-3,5-dimethylphenyl methylcarbamate | 1.25 |
| I | 4-(4-dimethylaminobenzylideneamino)-3,5-dimethylphenyl methylcarbamate | 7.5 |
| J | 4-(2,4-dichlorobenzylideneamino)-3,5-dimethylphenyl methylcarbamate | >8 |
| K | 4-benzylideneamino-3,5-dimethylphenyl methylcarbamate | >8 |
| L | 4-(2-methoxybenzylideneamino)-3,5-dimethylphenyl methylcarbamate | >8 |

The results of Table II clearly demonstrate the superior general systemic activity against bean aphids of 4-(2-hydroxybenzylideneamino)-3,5-dimethylphenyl methylcarbamate in comparison with the compounds within the scope of U.S. Pat. No. 3,012,068. 4-(2-Hydroxybenzylideneamino)-3,5-dimethylphenyl methylcarbamate exhibited a six-fold increase in general systemic activity against the bean aphid comparison with 4-(4-dimethylaminobenzylideneamino)-3,5-dimethylphenyl methylcarbamate and a greater than six-fold increase in general systemic activity against the bean aphid in comparison with 4-(2,4-dichlorobenzylideneamino)-3,5-dimethylphenyl methylcarbamate, 4-benzylideneamino-3,5-dimethylphenyl methylcarbamate and 4-(2-methoxybenzylideneamino)-3,5-dimethylphenyl methylcarbamate.

The results of examples in which compounds of this invention and the comparative compounds within the scope of U.S. Pat. No. 3,012,068 were tested for activity against the bean aphid, southern armyworm and Mexican bean beetle utilizing the bean aphid foilage spray test, the southern armyworm leaf spray test and the Mexican bean beetle leaf spray test are given below in Table III. The results are rated as follows: A=excellent control; B=partial control, and C=no control.

TABLE III

ACTIVITY AGAINST THE BEAN APHID, SOUTHERN ARMYWORM AND MEXICAL BEAN BEETLE (BEAN APHID FOLIAGE SPRAY TEST, SOUTHERN ARMYWORM LEAF SPRAY TEST, MEXICAN BEAN BEETLE LEAF SPRAY TEST)

| Example | Compound | Bean Aphid 500 ppm | Southern Armyworm 500 ppm | Mexican Bean Beetle 500 ppm |
|---|---|---|---|---|
| XXIII | 4-(2-hydroxybenzylideneamino)-3-methylphenyl methylcarbamate | C | A | A |
| XXIV | 4-(2-hydroxybenzylideneamino)-3,5-dimethylphenyl methylcarbamate | A | A | A |
| XXV | 4-(2-hydroxy-5-methoxybenzylideneamino)-3,5-dimethylphenyl methylcarbamate | A | A | A |
| XXVI | 4-(2-hydroxybenzylideneamino)-3-isopropylphenyl methylcarbamate | A | A | A |
| XXVII | 4-(5-bromo-2-hydroxybenzylideneamino-3-isopropylphenyl methylcarbamate | C | A | A |
| XXVIII | 4-(3,5-dibromo-2-hydroxybenzylideneamino)-3,5-dimethylphenyl methylcarbamate | B | A | A |
| XXIX | 4-(5-chloro-2-hydroxybenzylideneamino)-3,5-dimethylphenyl methylcarbamate | A | A | A |

TABLE III-continued
ACTIVITY AGAINST THE BEAN APHID, SOUTHERN ARMYWORM AND MEXICAL BEAN BEETLE
(BEAN APHID FOLIAGE SPRAY TEST, SOUTHERN ARMYWORM LEAF SPRAY TEST,
MEXICAN BEAN BEETLE LEAF SPRAY TEST)

| Example | Compound | Bean Aphid 500 ppm | Southern Armyworm 500 ppm | Mexican Bean Beetle 500 ppm |
|---|---|---|---|---|
| XXX | 4-(2-hydroxy-5-nitrobenzylideneamino)-3,5-dimethylphenyl methylcarbamate | A | A | A |
| XXXI | 4-(2-hydroxybenzylideneamino)-2-chloro-5-methylphenyl methylcarbamate | C | A | A |
| XXXII | 4-(2-hydroxybenzylideneamino)-naphth-1-yl methylcarbamate | C | A | A |
| XXXIII | 4-[1-(2-hydroxyphenyl)ethylideneamino]-3-methylphenyl methylcarbamate | C | A | A |
| XXXIV | 2,3-dihydro-2,2-dimethyl-4-(2-hydroxybenzylideneamino)-benzofuran-7-yl methylcarbamate | B | A | A |
| XXXV | 4-[2-hydroxy-4-(methylcarbamoyloxy)-benzylideneamino]-3,5-dimethylphenyl methylcarbamate | A | A | A |
| XXXVI | 3-isopropyl-4-(2-hydroxy-1-naphthylmethyleneamino)-phenyl methylcarbamate | C | A | A |
| XXXVII | 4-(2-hydroxybenzylideneamino)-3,5-dimethylphenyl methylcarbamate, copper (II) salt | C | A | A |
| XXXVIII | di[4-(2-hydroxybenzylideneamino)-3,5-dimethylphenyl] thiobis(methylcarbamate) | B | A | A |
| XXXIX | di[4-(2-hydroxybenzylideneamino)-3,5-dimethylphenyl] dithiobis(methylcarbamate) | C | A | A |
| XL | 4-(2-hydroxybenzylideneamino)-3,5-dimethylphenyl N—(tert-butylthiosulfenyl)-N—methylcarbamate | A | A | A |
| XLI | 4-(2-hydroxybenzylideneamino)-3,5-dimethylphenyl N—(4-tert-butylphenylsulfenyl)-N—methylcarbamate | A | A | A |
| XLII | 4-(2-hydroxybenzylideneamino)-3,5-dimethylphenyl N—(di-butylaminosulfenyl)-N—methylcarbamate | A | A | A |
| M | 4-(2,4-dichlorobenzylideneamino)-3,5-dimethylphenyl methylcarbamate | C | A | A |
| N | 4-(4-dimethylaminobenzylideneamino)-3,5-dimethylphenyl methylcarbamate | A | A | A |
| O | 4-benzylideneamino-3,5-dimethylphenyl methylcarbamate | A | A | A |
| P | 4-(2-methoxybenzylideneamino)-3,5-dimethylphenyl methylcarbamate | C | C | C |

The results of Table III clearly demonstrate that selected compounds within the scope of this invention possess desirable broad spectrum activity against a variety of insects.

What is claimed is:

1. A compound of the formula:

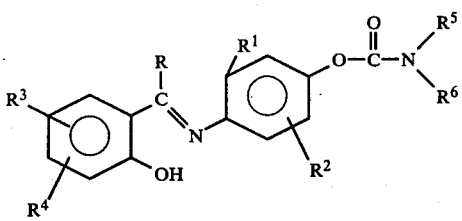

wherein R and $R^1$ are individually hydrogen or alkyl; $R^2$ is hydrogen, halo, alkyl, alkoxy, alkenyl, alkylthioalkyl or alkenyloxy provided that when $R^1$ and $R^2$ are individually alkyl or alkoxy and located adjacent to each other, then $R^1$ and $R^2$ together may form a three-to-five membered bridge consisting of carbon atoms or carbon and oxygen atoms in which the carbon atoms may be optionally substituted with alkyl and provided further that when the bridge consists of four carbon atoms, the resulting six-membered ring may optionally be aromatic or substituted aromatic; $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio provided that when $R^3$ and $R^4$ are individually alkyl and located adjacent to each other, then $R^3$ and $R^4$ together may form a three-to-five membered bridge consisting of carbon atoms in which the carbon atoms may be optionally substituted with alkyl and provided further than when the bridge consists of four carbon atoms, the resulting six-membered ring may optionally be aromatic or substituted aromatic; and $R^5$ and $R^6$ are individually hydrogen or alkyl provided that when $R^5$ is alkyl, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl hydroxyarylalkyleneaminoaryloxycarbonylaminosulphenyl, hydroxy arylalkyleneamino-aryloxycarbonylaminothiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination; and metal salts thereof.

2. A compound according to claim 1 wherein R and $R^1$ are individually hydrogen or alkyl having from 1 to 6 carbon atoms inclusive.

3. A compound according to claim 1 wherein R is hydrogen or methyl.

4. A compound according to claim 1 wherein $R^1$ is hydrogen, methyl or isopropyl.

5. A compound according to claim 1 wherein $R^2$ is hydrogen, halo or alkyl, alkoxy, alkenyl, alkylthioalkyl or alkenyloxy having from 1 to 6 carbon atoms inclusive.

6. A compound according to claim 1 wherein $R^2$ is hydrogen, chloro, methyl or isopropyl.

7. A compound according to claim 1 wherein when $R^1$ and $R^2$ are alkyl or alkoxy having from 1 to 6 carbon atoms inclusive and located adjacent to each other, then $R^1$ and $R^2$ together may form a three-to-five membered bridge consisting of carbon atoms or carbon and oxygen atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic.

8. A compound according to claim 1 wherein when $R^1$ and $R^2$ are alkyl or alkoxy having from 1 to 6 carbon atoms inclusive and located adjacent to each other, then $R^1$ and $R^2$ together form a three-membered bridge consisting of two carbon atoms and one oxygen atom in which the carbon atoms may optionally be substituted with methyl.

9. A compound according to claim 1 wherein when $R^1$ and $R^2$ are alkyl and located adjacent to each other, then $R^1$ and $R^2$ together form a four-membered bridge consisting of carbon atoms and the resulting six-membered ring is aromatic.

10. A compound according to claim 1 wherein $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio having from 1 to 6 carbon atoms inclusive.

11. A compound according to claim 1 wherein $R^3$ is hydrogen, bromo, chloro, nitro or methoxy.

12. A compound according to claim 1 wherein $R^4$ is hydrogen or methylcarbamoyloxy.

13. A compound according to claim 1 wherein when $R^3$ and $R^4$ are individually alkyl having from 1 to 6 carbon atoms inclusive and located adjacent to each other, then $R^3$ and $R^4$ together may form a bridge of from three to five carbon atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic.

14. A compound according to claim 1 wherein when $R^3$ and $R^4$ are alkyl and located adjacent to each other, then $R^3$ and $R^4$ together form a four-membered bridge consisting of carbon atoms and the resulting six-membered ring is aromatic.

15. A compound according to claim 1 wherein $R^5$ and $R^6$ are individually hydrogen or alkyl having from 1 to 6 carbon atoms inclusive provided that when $R^5$ is alkyl having from 1 to 6 carbon atoms inclusive, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoaryloxycarbonylaminosulfenyl, hydroxyarylalkyleneaminoaryloxycarbonylaminothiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination.

16. A compound according to claim 1 wherein when $R^5$ is methyl, then $R^6$ is hydrogen, 4-(2-hydroxybenzylideneamino)-3,5-dimethylphenoxycarbonyl(N-methylamino)-sulfenyl, 4-(2-hydroxybenzylideneamino)-3,5-dimethylphenoxycarbonyl(N-methylamino)thiosulfenyl, tert-butylthiosulfenyl, tert-butylphenylsulfenyl or dibutylaminosulfenyl.

17. A compound according to claim 1 wherein the metal salts thereof are selected from the group consisting of sodium, potassium, lithium, magnesium, calcium, molybdenum, chromium, aluminum, manganese, iron, cobalt, nickel, copper and zinc salts.

18. A compound according to claim 1 wherein the metal salt thereof is copper (II) salt.

19. 4-(2-Hydroxybenzylideneamino)-3,5-dimethylphenyl methylcarbamate.

20. 4-(2-Hydroxy-5-methoxybenzylideneamino)-3,5-dimethylphenyl methylcarbamate.

21. 4-(2-Hydroxybenzylideneamino)-3-isopropylphenyl methylcarbamate.

22. 4-(3,5-Dibromo-2-hydroxybenzylideneamino)-3,5-dimethylphenyl methylcarbamate.

23. 4-(5-Chloro-2-hydroxybenzylideneamino)-3,5-dimethylphenyl methylcarbamate.

24. 4-(2-Hydroxy-5-nitrobenzylideneamino)-3,5-dimethylphenyl methylcarbamate.

25. Di[4-(2-hydroxybenzylideneamino)-3,5-dimethylphenyl]thiobis(methylcarbamate).

26. 2,3-Dihydro-2,2-dimethyl-4-(2-hydroxybenzylideneamino)benzofuran-7-yl methylcarbamate.

27. 4-[2-Hydroxy-4-(methylcarbamoyloxy)benzylideneamino]-3,5-dimethylphenyl methylcarbamate.

28. 4-(2-Hydroxybenzylideneamino)-3,5-dimethylphenyl N-(4-tert-butylphenylsulfenyl)-N-methylcarbamate.

29. 4-(2-Hydroxybenzylideneamino)-3,5-dimethylphenyl N-(tert-butylthiosulfenyl)-N-methylcarbamate.

30. 4-(2-Hydroxybenzylideneamino)-3,5-dimethylphenyl methylcarbamate, copper (II) salt.

31. An insecticidal composition comprising an acceptable carrier and as the active toxicant an insecticidally effective amount of a compound of the formula:

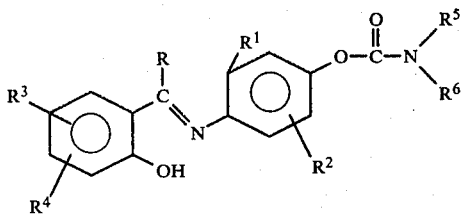

wherein R and $R^1$ are individually hydrogen or alkyl; $R^2$ is hydrogen, halo, alkyl, alkoxy, alkenyl, alkylthioalkyl or alkenyloxy provided that when $R^1$ and $R^2$ are individually alkyl or alkoxy and located adjacent to each other, then $R^1$ and $R^2$ together may form a three-to-five-membered bridge consisting of carbon atoms or carbon and oxygen atoms in which the carbon atoms may be optionally substituted with alkyl and provided further that when the bridge consists of four carbon atoms, the resulting six-membered ring may optionally be aromatic or substituted aromatic; $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio provided that when $R^3$ and $R^4$ are individually alkyl and located adjacent to each other, then $R^3$ and $R^4$ together may form a three-to-five membered bridge consisting of carbon atoms in which the carbon atoms may be optionally substituted with alkyl and provided further that when the bridge consists of four carbon atoms, the resulting six-membered ring may optionally be aromatic or substituted aromatic; and $R^5$ and $R^6$ are individually hydrogen or alkyl provided that when $R^5$ is alkyl, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoaryloxycarbonylaminosulfenyl, hydroxyarylalkyleneaminoaryloxycarbonylaminothiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination; and metal salts thereof.

32. A composition according to claim 31 wherein R and $R^1$ are individually hydrogen or alkyl having from 1 to 6 carbon atoms inclusive.

33. A composition according to claim 31 wherein R is hydrogen or methyl.

34. A composition according to claim 31 wherein $R^1$ is hydrogen, methyl or isopropyl.

35. A composition according to claim 31 wherein $R^2$ is hydrogen, halo or alkyl, alkoxy, alkenyl, alkylthioalkyl or alkenyloxy having from 1 to 6 carbon atoms inclusive.

36. A composition according to claim 31 wherein $R^2$ is hydrogen, chloro, methyl or isopropyl.

37. A composition according to claim 31 wherein when $R^1$ and $R^2$ are alkyl or alkoxy having from 1 to 6 carbon atoms inclusive and located adjacent to each other, then $R^1$ and $R^2$ together may form a three-to-five-membered bridge consisting of carbon atoms or carbon and oxygen atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic.

38. A composition according to claim 31 wherein when $R^1$ and $R^2$ are alkyl or alkoxy having from 1 to 6 carbon atoms inclusive and located adjacent to each other, then $R^1$ and $R^2$ together form a three-membered bridge consisting of two carbon atoms and one oxygen atom in which the carbon atoms may optionally be substituted with methyl.

39. A composition according to claim 31 wherein when $R^1$ and $R^2$ are alkyl and located adjacent to each other, then $R^1$ and $R^2$ together form a four-membered bridge consisting of carbon atoms and the resulting six-membered ring is aromatic.

40. A composition according to claim 31 wherein $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio having from 1 to 6 carbon atoms inclusive.

41. A composition according to claim 31 wherein $R^3$ is hydrogen, bromo, chloro, nitro or methoxy.

42. A composition according to claim 31 wherein $R^4$ is hydrogen or methylcarbamoyloxy.

43. A composition according to claim 31 wherein when $R^3$ and $R^4$ are individually alkyl having from 1 to 6 carbon atoms inclusive and located adjacent to each other, then $R^3$ and $R^4$ together may form a three-to-five membered bridge consisting of carbon atoms in which the carbon atoms may be optionally substituted with alkyl having from 1 to 4 carbon atoms inclusive and provided further than when the bridge consists of four carbon atoms, the resulting six-membered ring may optionally be aromatic or substituted aromatic.

44. A composition according to claim 31 wherein when $R^3$ and $R^4$ are alkyl and located adjacent to each other, then $R^3$ and $R^4$ together form a four-membered bridge consisting of carbon atoms and the resulting six-membered ring is aromatic.

45. A composition according to claim 31 wherein $R^5$ and $R^6$ are individually hydrogen or alkyl having from 1 to 6 carbon atoms inclusive provided that when $R^5$ is alkyl having from 1 to 6 carbon atoms inclusive, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoaryloxycarbonylaminosulfenyl, hydroxyarylalkyleneaminoaryloxycarbonylaminothiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination.

46. A composition according to claim 31 wherein when $R^5$ is methyl, then $R^6$ is hydrogen, 4-(2-hydroxybenzylideneamino)-3,5-dimethylphenoxycarbonyl(N-methylamino)sulfenyl, 4-(2-hydroxybenzylideneamino)-3,5-dimethylphenoxycarbonyl(N-methylamino)-thiosulfenyl, tert-butylthiosulfenyl, tert-butylphenylsulfenyl or dibutylaminosulfenyl.

47. A composition according to claim 31 wherein the metal salts of the active toxicant are selected from the group consisting of sodium, potassium, lithium, magnesium, calcium, molybdenum, chromium, aluminum, manganese, iron, cobalt, nickel, copper and zinc salts.

48. A composition according to claim 31 wherein the metal salt of the active toxicant is copper (II) salt.

49. A composition according to claim 31 wherein the active toxicant is 4-(2-hydroxybenzylideneamino)-3,5-dimethylphenyl methylcarbamate.

50. A composition according to claim 31 wherein the active toxicant is 4-(2-hydroxy-5-methoxybenzylideneamino)-3,5-dimethylphenyl methylcarbamate.

51. A combination according to claim 31 wherein the active toxicant is 4-(2-hydroxybenzylideneamino)-3-isopropylphenyl methylcarbamate.

52. A composition according to claim 31 wherein the active toxicant is 4-(3,5-dibromo-2-hydroxybenzylideneamino)-3,5-dimethylphenyl methylcarbamate.

53. A composition according to claim 31 wherein the active toxicant is 4-(5-chloro-2-hydroxybenzylideneamino)-3,5-dimethylphenyl methylcarbamate.

54. A composition according to claim 31 wherein the active toxicant is 4-(2-hydroxy-5-nitrobenzylideneamino)-3,5-dimethylphenyl methylcarbamate.

55. A composition according to claim 31 wherein the active toxicant is di[4-(2-hydroxybenzylideneamino)-3,5-dimethylphenyl]thiobis(methylcarbamate).

56. A composition according to claim 31 wherein the active toxicant is 2,3-dichloro-2,2-dimethyl-4-(2-hydroxybenzylideneamino)benzofuran-7-yl methylcarbamate.

57. A composition according to claim 31 wherein the active toxicant is 4-[2-hydroxy-4-(methylcarbamoyloxy)benzylideneamino]-3,5-dimethylphenyl methylcarbamate.

58. A composition according to claim 31 wherein the active toxicant is 4-(2-hydroxybenzylideneamino)-3,5-dimethylphenyl N-(4-tert-butylphenylsulfenyl)-N-methylcarbamate.

59. A composition according to claim 31 wherein the active toxicant is 4-(2-hydroxybenzylideneamino)-3,5-dimethylphenyl N-(tert-butylthiosulfenyl)-N-methylcarbamate.

60. A composition according to claim 31 wherein the active toxicant is 4-(2-hydroxybenzylideneamino)-3,5-dimethylphenyl methylcarbamate, copper (II) salt.

61. A method of controlling insects which comprises subjecting them to an insecticidally effective amount of a compound of the formula:

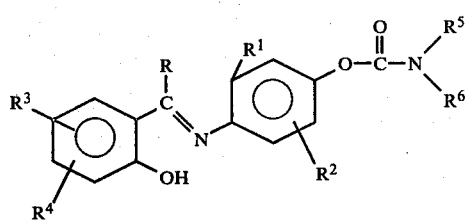

wherein R and $R^1$ are individually hydrogen or alkyl; $R^2$ is hydrogen, halo, alkyl, alkoxy, alkenyl, alkylthioalkyl or alkenyloxy provided that when $R^1$ and $R^2$ are individually alkyl or alkoxy and located adjacent to each other, then $R^1$ and $R^2$ together may form a three-to-five-membered bridge consisting of carbon atoms or carbon and oxygen atoms in which the carbon atoms may be optionally substituted with alkyl and provided further that then the bridge consists of four carbon atoms, the resulting six-membered ring may optionally be aromatic or substituted aromatic; $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio provided that when $R^3$ and $R^4$ are individually alkyl and located adjacent to each other, then $R^3$ and $R^4$ together may form a three-to-five-membered bridge consisting of carbon atoms in which the carbon atoms may be optionally substituted with alkyl and provided further that when the bridge consists of four carbon atoms, the resulting six-membered ring may optionally be aromatic or substituted aromatic; and $R^5$ and $R^6$ are individually hydrogen or alkyl provided that when $R^5$ is alkyl, then $R^6$ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoaryloxycarbonylaminosulfenyl, hydroxyarylalkyleneaminoaryloxycarbonylaminothiosulfenyl, alkylsulfenyl, phenylsulfenyl, alkylthiosulfenyl or phenylthiosulfenyl wherein the permissible substituents are one or more fluoro, cholor, bromo, cyano, aroyl, nitro, alkyl, alkanoyl, alkoxy, phenyl, phenoxy or trihalomethyl substituents in any combination; and metal salts thereof.

62. A method according to claim 61 wherein R and $R^1$ are individually hydrogen or alkyl having from 1 to 6 carbon atoms inclusive.

63. A method according to claim 61 wherein R is hydrogen or methyl.

64. A method according to claim 61 wherein $R^1$ is hydrogen, methyl or isopropyl.

65. A method according to claim 61 wherein $R^2$ is hydrogen, halo or alkyl, alkoxy, alkenyl, alkylthioalkyl or alkenyloxy having from 1 to 6 carbon atoms inclusive.

66. A method according to claim 61 wherein $R^2$ is hydrogen, chloro, methyl or isopropyl.

67. A method according to claim 61 wherein when $R_1$ and $R_2$ are alkyl or alkoxy having from 1 to 6 carbon atoms inclusive and located adjacent to each other, then $R^1$ and $R^2$ together may form a three-to-five membered bridge consisting of carbon atoms or carbon and oxygen atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic.

68. A method according to claim 61 wherein when $R^1$ and $R^2$ are alkyl or alkoxy having from 1 to 6 carbon atoms inclusive and located adjacent to each other, then $R^1$ and $R^2$ together form a three-membered bridge consisting of two carbon atoms and one oxygen atom in which the carbon atoms may optionally be substituted with methyl.

69. A method according to claim 61 wherein when $R^1$ and $R^2$ are alkyl and located adjacent to each other, then $R^1$ and $R^2$ together form a four-membered bridge consisting of carbon atoms and the resulting six-membered ring is aromatic.

70. A method according to claim 61 wherein $R^3$ and $R^4$ are individually hydrogen, halo, nitro, cyano, hydroxy, unsubstituted or aliphatically substituted phenyl or phenoxy, alkyl, alkoxy, alkylcarbamoyloxy or alkylthio having from 1 to 6 carbon atoms inclusive.

71. A method according to claim 61 wherein $R^3$ is hydrogen, bromo, chloro, nitro or methoxy.

72. A method according to claim 61 wherein $R^4$ is hydrogen or methylcarbamoyloxy.

73. A method according to claim 61 wherein when $R^3$ and $R^4$ are individually alkyl having from 1 to 6 carbon atoms inclusive and located adjacent to each other, then R³ and R⁴ together may form a three-to-five-membered bridge consisting of carbon atoms in which the carbon atoms may be optionally substituted with alkyl having from 1 to 4 carbon atoms inclusive and provided further that when the bridge consists of four carbon atoms, the resulting six-membered ring may optionally be aromatic or substituted aromatic.

74. A method according to claim 61 wherein when R³ and R⁴ are alkyl and located adjacent to each other, then R³ and R⁴ together form a four-membered bridge consisting of carbon atoms and the resulting six-membered ring is aromatic.

75. A method according to claim 61 wherein R⁵ and R⁶ are individually hydrogen or alkyl having from 1 to 6 carbon atoms inclusive provided that when R⁵ is alkyl having from 1 to 6 carbon atoms inclusive, then R⁶ may also be alkanoyl, haloalkanoyl, haloalkylsulfenyl, dialkylaminosulfenyl, morpholinosulfenyl or either substituted or unsubstituted cycloalkylsulfenyl, cycloalkylthiosulfenyl, hydroxyarylalkyleneaminoaryloxycarbonylaminosulfenyl, hydroxyarylalkyleneaminoaryloxycarbonylaminothiosulfenyl, alkylsulfenyl, phenylsulfenyl, alkylthiosulfenyl or phenylthiosulfenyl wherein the permissible substituents are one or more fluoro, chloro, bromo, cyano, aroyl, nitro, alkyl, alkanoyl, alkoxy, phenyl, phenoxy or trihalomethyl substituents in any combination.

76. A method according to claim 61 wherein when R⁵ is methyl, then R⁶ is hydrogen, 4-(2-hydroxybenzylideneamino)-3,5-dimethylphenoxycarbonyl(N-methylamino)-sulfenyl, 4-(2-hydroxybenzylideneamino)-3,5-dimethylphenoxcarbonyl(N-methylamino)thiosulfenyl, tert-butylthiosulfenyl, tert-butylpenylsulfenyl or dibutylaminosulfenyl.

77. A method according to claim 61 wherein the metal salts of the compound are selected from the group consisting of sodium, potassium, lithium, magnesium, calcium, molybdenum, chromium, aluminum, manganese, iron, cobalt, nickel, copper and zinc salts.

78. A method according to claim 61 wherein the metal salt of the compound is copper (II) salt.

79. A method according to claim 61 wherein the compound is 4-(2-hydroxybenzylideneamino)-3,5-dimethylphenyl methylcarbamate.

80. A method according to claim 61 wherein the compound is 4-(2-hydroxy-5-methoxybenzylideneamino)3,5-dimethylphenyl methylcarbamate.

81. A method according to claim 61 wherein the compound is 4-(2-hydroxybenzylideneamino)-3-isopropylphenyl methylcarbamate.

82. A method according to claim 61 wherein the compound is 4-(3,5-dibromo-2-hydroxybenzylideneamino)-3,5-dimethylphenyl methylcarbamate.

83. A method according to claim 61 wherein the compound is 4-(5-chloro-2-hydroxybenzylideneamino)-3,5-dimethylphenyl methylcarbamate.

84. A method according to claim 61 wherein the compound is 4-(2-hydroxy-5-nitrobenzylideneamino)-3,5-dimethylphenyl methylcarbamate.

85. A method according to claim 61 wherein the compound is di[4-(2-hydroxybenzylideneamino)-3,5-dimethylphenyl]thiobis(methylcarbamate).

86. A method according to claim 61 wherein the compound is 2,3-dichloro-2,2-dimethyl-4-(2-hydroxybenzylideneamino)benzofuran-7-yl methylcarbamate.

87. A method according to claim 61 wherein the compound is 4-[2-hydroxy-4-(methylcarbamoyloxy)-benzylideneamino]-3,5-dimethylphenyl methylcarbamate.

88. A method according to claim 61 wherein the compound is 4-(2-hydroxybenzylideneamino)-3,5-dimethylphenyl-N-(4-tert-butylphenylsulfenyl)-N-methylcarbamate.

89. A method according to claim 61 wherein the compound is 4-(2-hydroxybenzylideneamino)-3,5-dimethylphenyl-N-(tert-butylthiosulfenyl)-N-methylcarbamate.

90. A method according to claim 61 wherein the compound is 4-(2-hydroxybenzylideneamino)-3,5-dimethylphenyl methylcarbamate, copper (II) salt.

* * * * *